United States Patent [19]
Liu

[11] Patent Number: 5,997,855
[45] Date of Patent: Dec. 7, 1999

[54] PERSONAL CARE COMPOSITION CONTAINING A CLEAR HOMOGENEOUS POLYMER OF AN N-VINYL LACTAM

[75] Inventor: Kou-Chang Liu, Wayne, N.J.

[73] Assignee: ISP Investments Inc., Wilmington, Del.

[21] Appl. No.: 09/014,465

[22] Filed: Jan. 28, 1998

Related U.S. Application Data

[63] Continuation-in-part of application No. 08/365,258, Dec. 28, 1994, Pat. No. 5,609,865, and a continuation-in-part of application No. 08/365,259, Dec. 28, 1994, Pat. No. 5,626,836, and a continuation-in-part of application No. 08/365,257, Dec. 28, 1994, Pat. No. 5,523,369.

[51] Int. Cl.$^6$ .......................... C08F 226/10; A61K 31/79
[52] U.S. Cl. .......................... 424/78.24; 526/264; 525/72
[58] Field of Search .................. 424/78.2, 78.24; 526/264, 328.5, 317.1, 318.4, 318.44, 307, 307.2, 307.6, 307.7, 279; 525/283, 244, 93, 95, 51, 72; 523/303, 305

Primary Examiner—Edward J. Webman
Attorney, Agent, or Firm—Marilyn J. Maue; William J. Davis

[57] ABSTRACT

A multicomponent homogeneous polymer of (a) from about 30 to about 90 wt. % of a N-vinyl lactam, (b) from about 5 to about 30 wt. % of a quaternized and/or non-quaternized aminoalkylacrylic -ester and/or -amide, (c) from about 0.5 to about 30 wt. % of an unsaturated monomer selected from the group consisting of an acrylic ester or amide having a $C_4$ to $C_{22}$ alkyl group, a $C_4$ to $C_{22}$ α-olefin, a $C_4$ to $C_{22}$ vinyl ether (VE) and a vinyl ester of a $C_2$ to $C_{22}$ carboxylic acid and (d) from about 1 to about 30 wt. % of an unsubstituted acrylic or methacrylic acid and/or an unsubstituted amide of said acrylic or methacrylic acid and optionally, (e) up to 20 wt. % of a mono- or di-functional polysiloxane; all monomers combined to form a 100% polymer composition of randomly distributed monomers for use in personal care formulations, particularly as a hair fixative where the clear, colorless and conditioning film forming properties of the polymer produces a silky, lustrous appearance to the hair and long lasting styling hold.

10 Claims, No Drawings

PERSONAL CARE COMPOSITION CONTAINING A CLEAR HOMOGENEOUS POLYMER OF AN N-VINYL LACTAM

This application is a continuation-in-part of U.S. Pat. No. 5,609,865, Ser. No. 365,258; U.S. Pat. No. 5,626,836, Ser. No. 365,259 and U.S. Pat. No. 5,523,369, Ser. No. 365,257; all filed on Dec. 28, 1994.

BACKGROUND OF THE INVENTION

1. Field of the Invention

This invention is directed to homogeneous N-vinyl lactam polymers of a component system involving at least four monomers in predetermined concentrations and in random distribution in the polymer structure to more uniformly diffuse the individual properties of each monomer.

2. Description of the Prior Art

Many synthetic polymers containing vinyl lactams are employed in hair and skin care applications of the prior art. Patents pertaining to this art are U.S. Pat. Nos. 3,914,403; 3,954,960; 4,039,734*; 4,057,533; 4,210,161; 4,223,009*; 4,586,518; 4,764,363; 4,834,968; 4,842,850; 4,902,499; 4,906,459; 4,923,694*; 4,963,348; 4,983,770; 5011,895; 5,015,708; 5,126,124*; 5,158,762*; 5,275,809*; 5,502,136; 5,523,369; 5,609,836; 5,609,865; WO 91/15186; WO 91/15185; EPA 412704 A2; EPA 412707 A1 and JP 57126409.

\* cited in a parent case

In addition to the parent cases of the present application, several U.S. patents disclose the use of a N-vinyl lactam, an alkylaminoalkyl (meth)acrylate or (meth)acrylamide as a polymer suitable for use in pharmaceutical and cosmetic arts, particularly for use in hair spray compositions. These patents are U.S. Pat. Nos. 3,910,862; 4,923,694; 5,045,617; 5,321,110; 5,492,988 and 5,637,296 and of these only U.S. Pat. No. 5,492,988; together with U.S. Pat. No. 5,684,105 and the above parent applications disclose a polymer having a homogeneous structure. However, the homogeneous polymers of the prior art lack the essential fourth monomer unit of the present invention which provides strong hair hold, hair body building and quick drying properties to the hair without sacrificing shine or soft, silky appearance.

The homogeneous polymer structure is achieved only by the method disclosed in said parent applications and in U.S. Pat. Nos. 5,492,988 and 5,684,105 whose teachings are incorporated herein by reference. The homogeneous polymerization process generally comprises monitoring the feed rate of the more active monomer species with the rate of consumption of the less active monomer species.

In accordance with the above discussion, it is an object of this invention to provide a new, clear and colorless polymer of homogeneous structure having additional benefits for cosmetic and personal care formulations.

Another object is to provide a hair body building homogeneous polymer for use in a hair fixative mousse or gel composition which polymer is quick drying and provides a firm but soft film for a more natural appearance.

Another object relates to the ability to adjust the degree of hair body and hold by the use of a clear homogeneous polymer.

Still another object is to provide a polymer having random distribution of monomer units in the polymer so as to substantially and uniformly distribute the properties of the individual monomers throughout the polymer while still maintaining clarity.

These and other benefits and uses of the present invention will become apparent from the following description and disclosure.

DEFINITIONS

For the purposes of this invention, the term "polymer" is intended to describe the polymer containing at least four distinct monomer unit species as more particularly defined hereinafter. The terms "acrylamide," "acrylate" and "acrylic", as used alone or in combined form, are intended to include the methacrylamide, methacrylate and methacrylic derivatives and visa versa. For example, "dimethylamino ethylmethacrylate" (DMAEMA) is intended to include dimethylamino ethylacrylate, alone or both in admixture unless otherwise indicated. Similarly, "dimethylamino propylmethacrylamide" (DMAPMA), includes dimethylamino propyl acrylamide, alone or both in admixture unless otherwise indicated.

A personal care concentrate of the present invention as used for example in a hair spray, hair styling mousse or gel, skin cream or body building shampoo formulation, is the present homogeneous polymer in an aqueous, aqueous-alcoholic or alcohol solvent wherein the concentration of the polymer is between about 0.1 and about 10 wt. %, preferably between about 0.5 and about 6 wt. %.

A 50–60% VOC (volatile organic compounds) pump hair spray composition is a solution or suspension of the present homogeneous polymer containing from about 1 to about 10% solids, preferably from about 2 to about 5.5% solids, in 60% or less solvent, such as an alcohol, e.g. ethanol, the remainder being water and excipients at the option of the formulator but preferably contains a corrosion inhibitor.

A 50–60% VOC aerosol hair spray of this invention contains between about 1 and about 10% solids, preferably between about 2 and about 4% solids, in a microsuspension of the homogeneous polymer, 20% or less alcohol, preferably ethanol, and 35% or less propellant, e.g. dimethyl ether. Generally the composition also contains a neutralizer and other excipients as well as a corrosion inhibitor, e.g. ethoxylated butynediol, a thioester, and the like.

SUMMARY OF THE INVENTION

In accordance with this invention there is provided a homogeneous polymer of (a) from about 30 to about 90 wt. % of a N-vinyl lactam, (b) from about 5 to about 30 wt. % of a quaternized and/or non-quaternized aminoalkylacrylic -ester and/or -amide, (c) from about 0.5 to about 30 wt. % of a coreactive unsaturated monomer selected from the group consisting of an acrylic ester or amide containing a $C_4$ to $C_{22}$ alkyl group, a $C_4$ to $C_{22}$ a-olefin, a $C_4$ to $C_{22}$ vinyl ether and a vinyl ester of a $C_2$ to $C_{22}$ carboxylic acid and (d) from about 1 to about 30 wt. % of an unsubstituted acrylic acid or an unsubstituted amide thereof and optionally (e) up to about 20 wt. % of a mono- or di-functional polymerizable polysiloxane monomer (MVPS) and (DVPS) respectively.

The polymers of this invention have a weight average molecular weight of from about 10,000 to about 5,500,000 and a Hack Turbidity preferably less than 5.

The N-vinyl lactam components of the polymer, e.g. N-vinyl pyrrolidone (VP) and N-vinyl caprolactam (VCL), optionally contain one or two $C_1$ to $C_4$ alkyl groups substituted on the heterocyclic ring and may also include mixtures of such lactams within the group or with unsubstituted lactam.

DETAILED DESCRIPTION OF THE INVENTION

Within the broad definition of the present polymer, the preferred homogeneous polymer of this invention contains, as the first component, from about 40 to about 85 wt. % of the N-vinyl lactam moiety, most preferably from 60 to 80 wt. %. The N-vinyl lactam component comprises from 0 to 100% VP, from 0 to 100% VCL or mixtures of these monomers; these monomers being most preferably unsubstituted. When a mixture of VP and VCL is employed, a mole ratio of between about 5:1 and about 1:5 is preferred.

The second quaternized or non-quaternized amino component of the polymer is preferably present at a concentration of from about 10 to about 30 wt. % and is an acrylate or acrylamide defined by the formula:

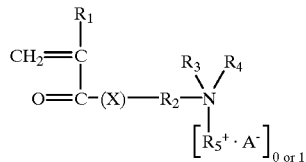

wherein $R_1$ is hydrogen or methyl; $R_2$ is $C_2$ to $C_{20}$ alkylene; X is oxygen or

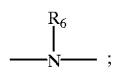

$R_6$, $R_3$ and $R_4$ are each independently hydrogen or $C_1$ to $C_4$ alkyl; $R_5$ is $C_2$ to $C_4$ alkyl and A is any anion including a halide, sulfate, sulfonate, phosphate, tosylate and the like. As the second (b) component, mixtures of quaternized and non-quaternized compounds are included as well as mixtures of compounds designated by X such as mixtures of aminoalkyl acrylate and aminoalkylacrylamide in a quaternized or non-quaternized state. Particularly preferred species of (b) are the quaternized and non-quaternized dimethylamino propyl methacrylate, dimethylamino propylacrylate, dimethylamino ethylacrylate, 3-methyl acrylamidopropyl trimethyl ammonium chloride (MAPTAC), 3-methylacrylamido propyl dimethylethyl tosylate and dimethylamino propyl methacrylamide (DMAPMA).

The third component of the present polymer is preferably present at a concentration of from about 1 to about 20 wt. % and can be mixtures of species within the category. The preferred species of this group include 1-octadecene, vinyl acetate, vinyl propionate, vinyl neonondecanoate, vinyl neodeconate, vinyl pivalate, dodecyl vinyl ether, hexadecyl vinyl ether, octyl vinyl ether, dodecyl methacrylate (DDMA), octadecyl methacrylate (ODMA), hexadecyl acrylate, octyl methacrylamide, 2-ethylhexyl acrylamide, t-butyl acrylamide and mixtures thereof. The incorporation of this monomer provides a desirable flexible hold, quick dry, non-tacky, body building and other additional conditioning effects in hair fixative compositions.

The fourth component of the polymer is critical and is preferably employed at a concentration of from about 2 to about 25 wt. %, most preferably from about 5 and about 15 wt. % concentration and is unsubstituted and is (meth) acrylic acid or the unsubstituted amide thereof. The incorporation of this monomer is critical for achieving superior stiffness and longer lasting hold for hair styling applications and is essential in providing a polymer product which is uniformly distributed in a mousse or gel formulation for hair styling.

The fifth optional polysiloxane component is preferably employed at a concentration of from 0.5 to 20 wt. % for the monofunctional polysiloxane (MVPS) and from about 0.1 to about 5 wt. % for the difunctional polysiloxane (DVPS). The siloxane monomer is broadly described by the formula:

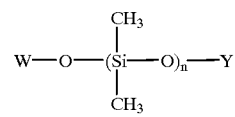

wherein
n has a value of from 1 to 100;
W is vinyl dimethyl silyl,

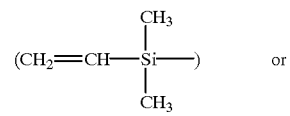 or methacryloxyalkyl dimethyl silyl,

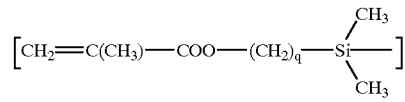

wherein q has a value of from 1 to 10, preferably 2 to 5, Y=W or Y is phenyl or $CH_3(CH_2)_p$ where p has a value from 0 to 6. Examples of the silyl monomers include mono- or di-methacryloxy propyl terminated polydimethyl siloxane, mono- or di-acryloxy propyl terminated polydimethylsiloxane and di-vinyl terminated polydimethylsiloxane. Incorporation of the siloxane moiety in the homogeneous polymer reinforces body building and luster and soft feel to hair while increasing combability. The polyfunctional siloxane introduces a degree of crosslinking in the polymer which further promotes hair body building properties and produces a firmer stronger hold.

The present polymer is generally prepared according to the homogeneous polymerization process disclosed in U.S. Pat. Nos. 5,492,988; 5,492,988; 5,684,105 and 5,626,836; the teachings of which is incorporated herein by reference. In summary, the process involves precharging the monomer having the lowest reactivity and initiator prior to the charge of major amounts of the remaining monomers having higher reactivity and controlling the gradual feed rate of the more reactive monomer species so that the relative concentrations of all monomer species remain constant throughout the polymerization reaction and the product at completion of the polymerization contains less than 0.1% unreacted VP and/or less than 0.1% unreacted VCL.

Suitable initiators for the homogeneous polymerization reaction are the conventional free radical types which include organic and inorganic compounds such as hydrogen peroxide, lauryl peroxide, t-butylperoxy pivalate (LUPERSOL® 11); t-amylperoxy pivalate (LUPERSOL® 554); dimethyl 2,5-di(t-butylperoxy) hexane (LUPERSOL® 101); azobis (butyronitrile); azobis (methylnitrile); azobis (diisobutyronitrile); azobis(isovaleronitrile); azobis (cyclohexanecarbonitrile) and the like.

The solution polymerization is carried out at a temperature of between about 50° and about 90° C., preferably between about 60° and about 80° C. for a period of from about 4 to about 100 hours, more conveniently from about 6 to about 30 hours or until the polymerization is completed by indication of the above trace amounts of residual monomer.

To obtain the present polymer having a homogeneous structure it is critical that part or all of the least reactive monomer be precharged into a reactor and that at least a major portion of the more reactive remaining monomers, be then introduced incrementally or continuously into the precharged reactor at such rates that allow the ratio of the relative concentrations of all monomers to remain constant throughout the reaction so that all monomers can react to form a substantially homogeneous polymer in a desired compositional ratio. Consequently, the substantially homogeneous polymer of this invention is obtained whose composition approaches the nominal monomer ratio of the desired polymer composition and whose structure has at least four individual monomeric unit groups of the copolymer distributed substantially uniformly in a homogeneous chain along the backbone of the polymer.

The precharge in the process of the invention may include some of the 2–5th component monomers, generally in an amount of up to about 30% of the total amount of second and third monomers required for a predetermined terpolymer composition without affecting the homogeneous polymerization process.

The schedule of addition to accomplish the desired matched rate of reaction is described in following Examples.

EXAMPLE 1

Preparation of a Homogeneous Tetrapolymer of

70% VP. 20% DMAPMA, 5% AA and 9% DDMA

Initially, vinylpyrrolidone (VP), dimethylaminopropyl methacrylamide (DMAPMA), acrylic acid (AA), dodecyl methacrylate (DDMA) and alcohol, e.g. ethanol, were charged into a two liter resin pot equipped with a gas inlet, a liquid inlet, a thermometer, a condenser and a mechanic stirrer. The solution was gradually heated to 78° C. and a stream of nitrogen was introduced which bubbled through the solution during the reaction to remove oxygen from the system. The remaining amounts of the monomers were then added to the solution according to the times shown in Table I, so that the relative concentrations of the component monomers remained practically constant throughout the reaction.

An ethanol solution of 2,2'-azobis(2-methylbutane-nitrile) (VAZO-67) initiator was added to the reaction pot as soon as the scheduled monomer feedings started, and a total of 4.4 g of the initiator solution was added in portions over 5.5 hours. The solution was held for an additional 5 hours at 78° C. to yield an ethanol solution of compositionally homogeneous copolymer of VCL/DMAPMA/AA/DDMA.

TABLE I

| Time (min) | VP (g) | DMAPMA (ml) | Acrylic Acid (ml) | $C_{12}MA$ (ml) | EtOH (ml) | Total (g) |
|---|---|---|---|---|---|---|
| 0 | 420 | 6.43 | 1.43 | 1.73 | 964.33 | 1186 |
| 0–30 | | 51.35 | 11.38 | 13.8 | 76.53 | 1317.94 |
| 30–60 | | 33.1 | 7.34 | 8.89 | 49.33 | 1402.98 |
| 60–90 | | 18.88 | 4.19 | 5.07 | 28.14 | 1451.49 |
| 90–120 | | 9.89 | 2.19 | 2.66 | 14.73 | 1476.89 |
| 120–150 | | 4.92 | 1.09 | 1.32 | 7.33 | 1489.53 |
| 150–180 | | 2.38 | 0.53 | 0.64 | 3.54 | 1495.64 |
| 180–210 | | 1.14 | 0.25 | 0.31 | 1.7 | 1498.57 |
| 210–240 | | 0.54 | 0.12 | 0.14 | 0.8 | 1499.95 |
| Total (g) | 420 | 120 | 30 | 30 | 900 | 1500 |

EXAMPLE 2

Example 1 was repeated except that 70% VP/17% MAPTAC/10% AA/3% ODMA monomers and methanol was substituted for the monomers and solvent in Example 1. Table II below shows the addition of monomers to achieve the homogeneous polymer product.

TABLE II

| Time (min) | VP (g) | MAPTAC (ml) | Acrylic Acid (ml) | $C_{18}MA$ (ml) | MeOH (g) | Total (g) |
|---|---|---|---|---|---|---|
| 0 | 420 | 9.69 | 2.85 | 1.04 | 798 | 1232.1 |
| 0–30 | | 38.42 | 11.31 | 4.13 | | 1288.02 |
| 30–60 | | 37.53 | 11.05 | 4.04 | | 1342.65 |
| 60–90 | | 30.76 | 9.05 | 3.31 | | 1387.42 |
| 90–120 | | 24.16 | 7.11 | 2.6 | | 1422.59 |
| 120–150 | | 17.67 | 5.2 | 1.9 | | 1448.31 |
| 150–180 | | 12.78 | 3.76 | 1.37 | | 1466.91 |
| 180–210 | | 9.08 | 2.67 | 0.98 | | 1480.13 |
| 210–240 | | 6.33 | 1.86 | 0.68 | | 1489.34 |
| 240–270 | | 4.34 | 1.28 | 0.47 | | 1495.66 |
| 270–300 | | 2.99 | 0.88 | 0.32 | | 1500.01 |
| Total (g) | 420 | 204 | 24 | 12 | 798 | 1500 |

EXAMPLE 3

Example 1 is repeated except that 70% VCL/17% DMAPMA/10% AA/3% ODMA monomers were substituted. The procedure for the addition of monomers to obtain the corresponding homogeneous polymer are substantially the same. EXAMPLE 4

Example 1 was repeated except that 40% VCL/26% VP/10% DMAPMA/10% AA/10% t-butyl ester of AA/4% DDMA was substituted.

Table III describes the addition of monomers to achieve the homogeneous multi component polymer product.

TABLE III

| Time (min) | VCL (g) | VP (ml) | DMAPMA (ml) | Acrylic Acid (ml) | tC$_4$AA (ml) | C$_{12}$MA (ml) | EtOH (ml) | Total (g) |
|---|---|---|---|---|---|---|---|---|
| 0 | 100 | 31.44 | 2.7 | 2.38 | 2.48 | 1.15 | 368.54 | 430.53 |
| 0–30 | | 18.13 | 5.03 | 4.46 | 4.65 | 2.16 | 34.44 | 492.38 |
| 30–60 | | 8.29 | 4.92 | 4.36 | 4.54 | 2.11 | 24.23 | 535.62 |
| 60–90 | | 3.35 | 4.03 | 3.57 | 3.72 | 1.73 | 16.41 | 564.76 |
| 90–120 | | 1.28 | 3.17 | 2.81 | 2.92 | 1.36 | 11.54 | 585.19 |
| 120–150 | | | 2.32 | 2.05 | 2.14 | 1 | 7.5 | 598.43 |
| 150–180 | | | 1.68 | 1.49 | 1.55 | 0.72 | 5.43 | 608.02 |
| 180–210 | | | 1.19 | 1.06 | 1.1 | 0.51 | 3.86 | 614.83 |
| 210–240 | | | 0.83 | 0.73 | 0.77 | 0.36 | 2.69 | 619.57 |
| 240–270 | | | 0.57 | 0.5 | 0.53 | 0.24 | 1.85 | 622.82 |
| 270–300 | | | 0.39 | 0.35 | 0.36 | 0.17 | 1.27 | 625.06 |
| Total (g) | 100 | 65 | 25 | 25 | 25 | 10 | 375 | 625 |

EXAMPLE 5

Example 1 was repeated except that 40% VCL/36% VP/15% DMAEMA/5% AA/4% DDMA was substituted.

Table IV describes the addition of monomers to achieve the homogeneous multicomponent polymer product.

TABLE IV

| Time (min) | VCL (g) | VP (ml) | DMAPMA (ml) | Acrylic Acid (ml) | C$_{12}$MA (ml) | EtOH (ml) | Total (g) |
|---|---|---|---|---|---|---|---|
| 0 | 72 | 31.35 | 2.89 | 0.86 | 0.81 | 462.8 | 472.21 |
| 0–30 | | 18.08 | 5.44 | 1.61 | 1.56 | 26.69 | 520.09 |
| 30–60 | | 8.27 | 5.31 | 1.57 | 1.53 | 16.68 | 549.72 |
| 60–90 | | 3.34 | 4.35 | 1.29 | 1.25 | 10.23 | 567.72 |
| 90–120 | | 1.28 | 3.42 | 1.01 | 0.98 | 6.69 | 579.41 |
| 120–150 | | | 2.5 | 0.74 | 0.72 | 3.96 | 586.25 |
| 150–180 | | | 1.81 | 0.53 | 0.52 | 2.86 | 591.19 |
| 180–210 | | | 1.28 | 0.38 | 0.37 | 2.03 | 594.7 |
| 210–240 | | | 0.9 | 0.26 | 0.26 | 1.42 | 597.15 |
| 240–270 | | | 0.61 | 0.18 | 0.18 | 0.97 | 598.83 |
| 270–300 | | | 0.42 | 0.13 | 0.12 | 0.67 | 599.99 |
| Total (g) | 72 | 64.8 | 27 | 9 | 7.2 | 420 | 600 |

EXAMPLE 6

Example 1 was repeated except that 70% VP/15% DMAEMA/10% AA/3% DDMA/2% vinyl terminated polysiloxane (PS-443) was substituted.

Table V describes the addition of monomers to achieve the homogeneous multicomponent polymer product.

EXAMPLE 7

Example 1 was repeated except that 66% VCL/20% DMAPMA/10% AA/4% DDMA was substituted.

Table VI describes the addition of monomers to achieve the homogeneous multicomponent polymer product.

TABLE V

| Time (min) | VP (g) | DMAEMA (ml) | Acrylic Acid (ml) | C$_4$MA (ml) | PS-443 Si (ml) | EtOH (ml) | Total (g) |
|---|---|---|---|---|---|---|---|
| 0 | 420 | 4.82 | 2.85 | 1.04 | 0.62 | 969.22 | 1189.84 |
| 0–30 | | 19.13 | 11.31 | 4.11 | 2.45 | 37 | 1254.48 |
| 30–60 | | 18.69 | 11.05 | 4.02 | 2.4 | 36.15 | 1317.65 |
| 60–90 | | 15.31 | 9.05 | 3.29 | 1.96 | 29.6.3 | 1369.4 |
| 90–120 | | 12.03 | 7.11 | 2.59 | 1.54 | 23.27 | 1410.06 |
| 120–150 | | 8.8 | 5.2 | 1.89 | 1.13 | 17.02 | 1439.8 |
| 150–180 | | 6.36 | 3.76 | 1.37 | 0.82 | 12.31 | 1461.31 |
| 180–210 | | 4.52 | 2.67 | 0.97 | 0.58 | 8.74 | 1476.58 |
| 210–240 | | 3.15 | 1.86 | 0.68 | 0.4 | 6.09 | 1487.22 |
| 240–270 | | 2.16 | 1.28 | 0.46 | 0.28 | 4.18 | 1494.52 |
| 270–300 | | 1.49 | 0.88 | 0.32 | 0.19 | 2.88 | 1499.55 |
| Total (g) | 420 | 90 | 60 | 18 | 12 | 900 | 1500 |

TABLE VI

| Time (min) | VCL (g) | DMAPMA (ml) | Acrylic Acid (ml) | $C_{12}MA$ (ml) | EtOH (ml) | Total (g) |
|---|---|---|---|---|---|---|
| 0 | 297 | 4.82 | 2.09 | 1.04 | 1185.57 | 1235.27 |
| 0–30 |  | 19.13 | 8.49 | 4.11 | 31.73 | 1290.53 |
| 30–60 |  | 18.69 | 8.3 | 4.02 | 31 | 1344.52 |
| 60–90 |  | 15.31 | 6.8 | 3.29 | 25.4 | 1388.75 |
| 90–120 |  | 12.03 | 5.34 | 2.59 | 19.95 | 1423.5 |
| 120–150 |  | 8.8 | 3.91 | 1.89 | 14.59 | 1448.92 |
| 150–180 |  | 6.36 | 2.83 | 1.37 | 10.56 | 1467.31 |
| 180–210 |  | 4.52 | 2.01 | 0.97 | 7.5 | 1480.37 |
| 210–240 |  | 3.15 | 1.4 | 0.68 | 5.22 | 1489.47 |
| 240–270 |  | 2.16 | 0.96 | 0.46 | 3.59 | 1495.71 |
| 270–300 |  | 1.49 | 0.66 | 0.32 | 2.47 | 1500.01 |
| Total (g) | 297 | 90 | 45 | 18 | 1050 | 1500 |

Representative applications of the present polymer are the following:

Hair Care Compositions

In a water-based, hair styling and conditioning composition, the homogeneous polymer of the invention comprises about 0.2–20%, preferably 1–10%, and, most preferably, about 2–8%, by weight of the hair care product, the rest being water, and, optionally including an organic solvent such as ethanol, and/or other acceptable excipient components such as corrosion inhibitors, silicones, surface active agents, viscosity modifiers, dyes, chelating agents, distributing aids, pearlescent aids, opacifiers, perfumes, fatty alcohols, pH adjusting agents, and the like.

The homogeneous polymer of the invention also finds particular utility in multifunctional hair care products such as water-based, rinse-off hair styling and conditioning products, and in leave-on hair care products such as a mousse, and may be included as a concentrate, or as a gel, and applied as a self-actuated pump hair spray, or in an aerosol product with a propellant. Various actuator and packaging devices known in the art may be used therewith.

Procedure for Preparing Hair Spray

Compositions of Invention

A. Pump Spray

The pump hair spray compositions of the invention were prepared by first dissolving the homogeneous polymer resin in ethanol and adding the requisite amount of water. The composition then was packaged into a high density polyethylene bottle fitted with a suitable pump actuator, e.g. a pump sprayer (160 ml) with 0.018×0.010 inch deep actuator (SEAQUIST EUROMIST II).

B. Aerosol Spray

The aerosol hair spray resin compositions of the invention were prepared from 65% by weight of the hair spray concentrate, a vapor phase inhibitor, a liquid phase inhibitor, adjuvants where needed, and 35% by weight of a propellant, e.g. dimethyl ether.

EXAMPLES 8–11

The following hair spray compositions of the invention were prepared in a stainless steel mixing vessel and mixed at ambient temperature for 20 minutes with a turbine agitator.

TABLE VII

HAIR SPRAY COMPOSITIONS

| Example No. Component | 8 | 9 | 10 | 11 |
|---|---|---|---|---|
|  | Weight % | | | |
| Homogeneous polymer of Ex. 1 (45% active in ethanol) | 8.90 | 6.67 | 8.90 | 6.67 |
| Water | 41.00 | 42.00 | 40.50 | 41.50 |
| Excipients |  |  | 0.50 | 0.50 |
| Propellant |  |  | 35.00 | 35.00 |
| Ethanol | 50.10 | 51.33 | 15.10 | 16.33 |
|  | 100.00 | 100.00 | 100.00 | 100.00 |

Comparative Example 12

The following comparative hair spray composition was prepared in the manner set forth above.

TABLE VIII

| Component | Weight % |
|---|---|
| Non-Homogeneous polymer of Ex. 1 (45% active in ethanol) | 8.90 |
| Water | 41.00 |
| Ethanol | 50.10 |

HAIR SPRAY PROPERTIES
INVENTION VS. COMPARATIVE EXAMPLE

|  | Homogeneous Composition (Ex. 8) | Non-Homogeneous Composition (Ex. 12) |
|---|---|---|
| Turbidity (HACH) | 0.6 | 40.1 |
| HHCR (90 min) | 88.6 | 84.2 |
| (4 hr.) | 76.6 | 75.3 |
| Particle size, DAV [V, 0.5] | 85.3 | 95.3 |
| Stiffness | 8.3 | 6.7 |
| Curl snap | 9.0 | 6.7 |
| Curl memory | 7.7 | 4.0 |

While the invention has been described with particular reference to certain embodiments thereof, it will be understood that many changes and modifications within the scope of the foregoing disclosure may be made which are within the sill of the art. Accordingly, it is intended to be bound only by the following claims, in which:

What is claimed is:

1. A homogeneous polymer of (a) from about 30 to about 90 wt. % of a N-vinyl lactam, (b) from about 5 to about 30 wt. % of a quaternized and/or non-quaternized aminoalkyl acrylate -ester and/or -amide, (c) from about 0.5 to about 30 wt. % of an unsaturated monomer selected from the group consisting of an acrylic ester or amide containing a $C_4$ to $C_{22}$ alkyl group, and (d) from about 1 to about 30 wt. % of an unsubstituted acrylic acid or an unsubstituted amide of said acrylic acid and optionally (e) up to 20 wt. % of a mono- or di-functional vinyl polysiloxane; all monomers combined in 100% composition.

2. The homogeneous polymer of claim 1 containing from about 40 to about 80 wt. % of (a), from about 10 to about 25 wt. % of (b), from about 1 to about 20 wt. % of (c) and from about 2 to about 25 wt. % of (d).

3. The homogeneous polymer of claim 1 containing (a), (b), (c), (d) and from about 0.1 to about 20 wt. % of (e).

4. The homogeneous polymer of claim 3 containing (a), (b), (c), (d) and from about 0.5 to about 5 wt. % of (e).

5. The homogeneous polymer of claim 1 containing (a), (b), (c) and (d) wherein the concentration of (a) is from about 60 to about 85 wt. %.

6. The homogeneous polymer of claim 1 of 100% composition containing (a), (b), c), (d) from about 0.1 to about 20 wt. % of a polysiloxane having the formula:

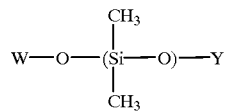

wherein W is vinyl dimethyl silyl or a methacryloxyalkyl dimethyl silyl group and Y is the same as W or is phenyl or $CH_3(CH_2)_p$ where p has a value of from 0 to 6.

7. The homogeneous polymer of claims 2 and 5 wherein (c) is octadecyl methacrylate.

8. The homogeneous polymer of claims 2 and 5 wherein (c) is dodecyl methacrylate.

9. A concentrate of the homogeneous polymer of claim 1 in an aqueous and/or alcoholic medium wherein the concentration of the polymer is between about 10 and about 70 wt. %.

10. The concentrate of claim 9 wherein the concentration of the polymer is between about 30 and about 55 wt. %.

* * * * *